United States Patent [19]

Hemming et al.

[11] Patent Number: 4,753,876
[45] Date of Patent: Jun. 28, 1988

[54] MARKER GENES IN PSEUDOMONAD BACTERIA

[75] Inventors: Bruce C. Hemming, Manchester; David J. Drahos, St. Louis, both of Mo.

[73] Assignee: Monsanto Company, St. Louis, Mo.

[21] Appl. No.: 592,158

[22] Filed: Mar. 21, 1984

[51] Int. Cl.$^4$ .................. C12Q 1/04; C12N 15/00; C12N 1/20; C12R 1/38
[52] U.S. Cl. .................. 435/34; 435/172.1; 435/172.3; 435/874; 935/84
[58] Field of Search .................. 435/4, 30, 34, 253, 435/874, 37, 172.1, 172.3; 935/84

[56] References Cited

U.S. PATENT DOCUMENTS

| | | | |
|---|---|---|---|
| 3,923,603 | 12/1975 | Chakrabarty et al. | 435/874 |
| 4,226,941 | 10/1980 | Goi et al. | 435/280 |
| 4,259,444 | 3/1981 | Chakrabarty | 435/253 |
| 4,452,894 | 6/1984 | Olsen et al. | 435/253 |
| 4,456,684 | 6/1984 | Weller et al. | 435/253 |
| 4,479,936 | 10/1984 | Vandenbergh et al. | 435/874 |
| 4,535,061 | 8/1985 | Chakrabarty et al. | 435/253 |

OTHER PUBLICATIONS

Baumberg et al. (1980) Journal of General Microbiology, vol. 119, pp. 257-262.
Lowe et al. (1975) Chemical Abstracts Item #4644z, vol. 83, No. 1, p. 413.
Barik et al. (1978) Antonie von Leeuwenhoek, vol. 44, pp. 171-176.
Marin et al., Aug. 1983, Journal of Food Protection, vol. 46, pp. 676-680.
Rudolph Hugh et al., Manual of Clinical Microbiology, Third Ed. (E. H. Lennette et al., eds.) pp. 288-317 (1980).
A. C. Hayward, Journal of Applied Bacteriology 43, pp. 407-411 (1977).
Bruce C. Hemming, "Plant-Associated Fluorescent Pseudomonads: Their Systematic Analysis, Microbial Antagonism and Iron Interaction:", PhD Thesis at Montana State Univ., Mar. 1982.

Primary Examiner—Sidney Marantz
Assistant Examiner—William J. Herald
Attorney, Agent, or Firm—Dennis R. Hoerner, Jr.; James W. Williams, Jr.

[57] ABSTRACT

This invention discloses the use of marker genes which do not involve antibiotics for environmental tracking of microorganisms. Such marker genes include chromogenic marker genes, and marker genes that allow a cell to proliferate on media containing a sole nutrient source which cannot be utilized by untransformed cells. Genetic transformation using such marker genes is used to create cells with two or more phenotypic traits that do not coexist in natural, untransformed cells. As one example, pseudonomad cells have been transformed with beta-galactosidase and lactose permease genes, to create cells which are (1) fluorescent, (2) able to hydrolyze X-gal or ONPG, and (3) capable of proliferation on lactose as a sole carbon source. Such cells are useful as soil inoculants, and their descendants can be tracked by using these characteristics. The marker genes may be placed under the control of inducible promoters.

11 Claims, 5 Drawing Sheets

MARKER GENES IN PSEUDOMONAD BACTERIA

TECHNICAL FIELD

This invention is in the fields of soil bacteria and genetic engineering.

BACKGROUND OF THE INVENTION

Microorganisms which inhabit the soil are of substantial importance to plant scientists and the agricultural industry. Many such microorganisms have beneficial effects; for example, the roots of most legumes develop nodules which are colonized by nitrogen-fixing bacteria. Such bacteria convert atmospheric nitrogen ($N_2$) into other forms of nitrogen such as ammonia and urea, which plants can utilize. Such legumes usually do not require nitrogen-containing fertilizers.

However, some soil microorganisms have detrimental effects upon plants. For example, numerous types of soil fungi hinder the germination of seeds and slow the growth of seedlings. Also, various types of soil bacteria cause plant roots to shrivel, and cause abnormal plant development or plant tumors such as hairy root disease and crown gall disease.

An important concept in rhizobiology (the biology of soil, roots, etc.) relates to microbial competition. See, e.g., Cook 1983 (note: a list of references with full citations is contained after the examples). Different microbes in any given area compete with each other for nutrients and energy sources This competition leads to a continually changing balance in the population of different bacterial and fungal types. It is very difficult to accurately analyze soil microbial competition over an area that is large enough to reflect the conditions in an entire field, and it is also difficult to create accurate models of soil microbial competition under controlled conditions in a laboratory or greenhouse. The difficulty of studying soil microbial competition is greatly increased by several factors, including (a) the great difficulty in adequately differentiating between different but similar strains, species, and genera of microorganisms, and (b) the inability of a scientist to determine whether a certain culture of a microorogism in a field descended from a different culture elsewhere in the field, (c) the ability of microorganisms to exchange genes, particularly under conditions of competitive stress. In addition, culture media developed for laboratory use is capable of culturing only a very small fraction (estimated to be less than 1%) of the microorganisms actually present in a soil sample, as indicated by direct microscopic examination; see Alexander 1977, Chapter 2. For example, nutrient broth is toxic to some types of soil microorganisms.

Marker Genes

To aid in their studies of bacterial transformation, gene expression, gene inheritance, and microbial competition, scientists have developed a variety of "marker genes," i.e., DNA sequences which confer an identifiable genotypic or preferably phenotypic trait upon their host cells. Various types of marker genes include antibiotic resistance genes, chromogenic genes, and morphology genes.

In the past, efforts to "track" soil microorganisms i.e., to follow their pattern of colonization in a field in competition with other microorganisms) have relied primarily upon certain genes which render the microorganisms resistant to certain antibiotics or toxins. For example, the most commonly used genes which have been used to track bacteria of the genus Pseudomonas provide resistance to rifampicin or nalidixic acid. See, e.g., Kloepper 1981. However, the use of antibiotic-resistance genes to track soil microorganisms suffers from several limitations, including the following:

1. Many types of soil bacteria have natural resistance to various antibiotics, including rifampicin and nalidixic acid. This can confuse results when certain antibiotics are used, or when the number of marked bacteria is low in relation to the native population, or when strains are genetically marked against only one antibiotic.

2. Some genes which confer resistance to certain antibiotics do so by systemic effects other than the expression of an enzyme which can detoxify a particular antibiotic. For example, bacteria which are resistant to rifampicin or nalidixic acid have significant alterations in their mechanisms of DNA transcription and replication. This may affect their ability to compete in the rhizosphere.

3. Many enzymes which detoxify certain antibiotics (such as kanamycin or streptomycin) can also affect various other substrates. This may significantly alter certain anabolic or catabolic pathways within the microorganism.

A variety of chromogenic marker genes and their use for laboratory and fermentation purposes have been described in the literature. As used herein, a "chromogenic marker gene" refers to a gene which encodes a protein, the presence of which can be conveniently detected due to a color change which occurs if the protein metabolizes a selected substrate. One such chromogenic marker gene is the *E. coli* lacZ gene, which encodes one form of an enzyme, $\beta$-galactosidase (B-gal); see Miller 1978. A variety of different chromogenic substrates can be used to indicate whether a colony of *E. coli* cells contains a functioning lacZ gene, including:

1. X-gal, a common name for 5-bromo-4-chloro-3-indolyl-$\beta$-D-galactopyranoside (Boehringer-Mannheim, Indianapolis, Ind.). If grown on suitable media containing X-gal, B-gal+ colonies of *E. coli* are blue in normal light, while B-gal− colonies are normally white. White B-gal− colonies can be either colonies which do not contain functioning lacZ genes, or colonies which contain lacZ genes under the control of a promoter which is repressed.

2. lac-MacConkey indicator plates which, if inoculated with *E. coli* cells, generate red B-gal+ colonies and white B-gal− colonies.

3. ONPG, which stands for ortho-nitrophenylgalactosidase. When ONPG (a clear substance) is hydrolysed by B-gal activity, o-nitrophenol is liberated which produces a visible yellow color.

Numerous proteins have been used in various types of chromogenic assays. However, only a very few genes which encode such proteins have been used as marker genes in the transformation of microorganisms, including the catechol dioxygenase gene (Zukowski 1983).

In addition, identificaion of certain clinically important microorganisms has been accomplished by using labeled (e.g., radioactive or enzyme linked) DNA probes which can anneal to DNA sequences in the microorganisms. For example, a DNA probe kit for identifying Salmonella bacteria is marketed by Integrated Genetics (Framingham, Mass.). This type of analysis usually involves a procedure similar to a Southern blot analysis (Southern 1975). Such analyses are more difficult, time-consuming, and expensive than analyses of entire colonies using chromogenic markers.

Fluorescent Pseudomonads

Various species of pseudomonad bacteria have been identified which exhibit fluorescent characteristics. These species create molecules, most of which are referred to as "siderophores", which are fluorescent; when these molecules (and the bacteria which contain them) are excited by light at a wavelength of about 290–390 nm (in the ultraviolet range), they emit light at a different wavelength, usually about 398–498 nm (in the yellow-green range). Fluorescent pseudomonads therefore can be easily distinguished from non-fluorescent pseudomonads by observing them under ultraviolet light. See, e.g., Meyer 1978 and Shelly 1980.

Fluorescent pseudomonads are of particular interest to plant scientists for several reasons. They are relatively abundant in the soil, and are widely associated with roots. In addition, various siderophores are believed to exert growth-inhibiting effects on some detrimental microorganisms, including pathogenic fungi. By impeding detrimental microorganisms, fluorescent pseudomonads have been shown to help protect seeds and seedlings in greenhouse conditions. Knowledge about whether (and to what extent) fluorescent pseudomonads can truly benefit plants in field conditions, and the selection and development of strains having maximum beneficial effects, would be greatly aided by more sophisticated analytical tools.

Fluorescent pseudomonads are also of scientific and industrial interest in various other fields of technology, including the biodegradation of agricultural and industrial wastes. See, e.g., U.S. Pat. No. 4,259,444 (Chakrabarty 1981).

However, some species of fluorescent pseudomonads have deterimental effects in some situations. For example, Ps. aeruginosa is a human pathogen, and Ps. syringae is a plant pathogen. The ability to track such pathogenic microorgansims in various environments would be a valuable aid in developing methods, substances, and even competing microorganisms to aid in their control.

At least one item of prior art, Baumberg 1980, described the transformation of two species of fluorescent pseudomonads using plasmids containing lactose-related genes. However, that publication indicated that one of the species transformed was capable of B-gal activity prior to the transformation. In addition, that publication was limited to an analysis of expression characteristics, and did not discuss any potential beneficial uses of the genes or the transformed cells.

The object of this invention is to provide an improved method for analyzing and tracking microorganisms and microbial genes in open environments. In particular, this invention provides a method for analyzing the fate and colonizing ability of soil microorganisms under field conditions of microbial competition.

SUMMARY OF THE INVENTION

This invention relates to the use of nonantibiotic marker genes to track microorganisms in open environments. Such genes may be used in microorganisms which have two co-existing characteristics:

1. the presence of a first easily detectable phenotypic characteristic, such as fluorescense or the ability to metabolize a particular substrate; and, 2. the absence of one or more second phenotypic characteristics other than antibiotic resistance which can be modified by the insertion of one or more selected genes into the microorganism.

The selected gene(s) are used to transform the microorganism thereby creating a culture of microorganisms which contain two or more phenotypic characteristics which do not coexist in any naturally occurring cell types found in a target environment. The transformed culture of microorganisms is inoculated into a selected environment. After a desired period of time, microorganisms are collected from the environment. Descendants of the inoculated cells are distinguished from other cells in the environment by determining whether a cell contains a combination of phenotypic characteristics that do not co-exist naturally.

Despite contrary teachings in the prior art, it has been discovered that all species of fluorescent pseudomonad bacteria subjected to careful analysis are incapable of proliferation on media containing lactose as a sole carbon source. Based upon this discovery, various species of fluorescent pseudomonads were transformed with plasmids containing the lactose-permease (lacY) and lactose-catabolizing (lacZ) genes from E. coli. When the transformed pseudomonad cells were plated on media containing the chromogenic substrate X-gal, colonies turned dark blue. When viewed under ultraviolet light, a transformed colony which normally appeared fluorescent yellow appeared as a fluorescent turquoise-blue colony.

In addition, fluorescent pseudomonads which were transformed with lacY and lacZ became capable of growth on culture medium which contains lactose as the sole carbon source. Since other fluorescent pseudomonads cannot easily transport or utilize lactose, this allows the marker genes of this invention to be used as selectable markers when tracking transformed fluorescent pseudomonads in the environment. This is particularly valuable when the number of genetically marked bacterial cells is low in relation to the native population.

This invention also relates to the use of inducible expression of non-antibiotic marker genes to track microorganisms. It also relates to the simultaneous use expression vetors having similar non-antibiotic coding sequences under the control of different regulatory sequences which provide distinguishable induction characteristics.

DETAILED DESCRIPTION OF THE INVENTION

Figure 1:
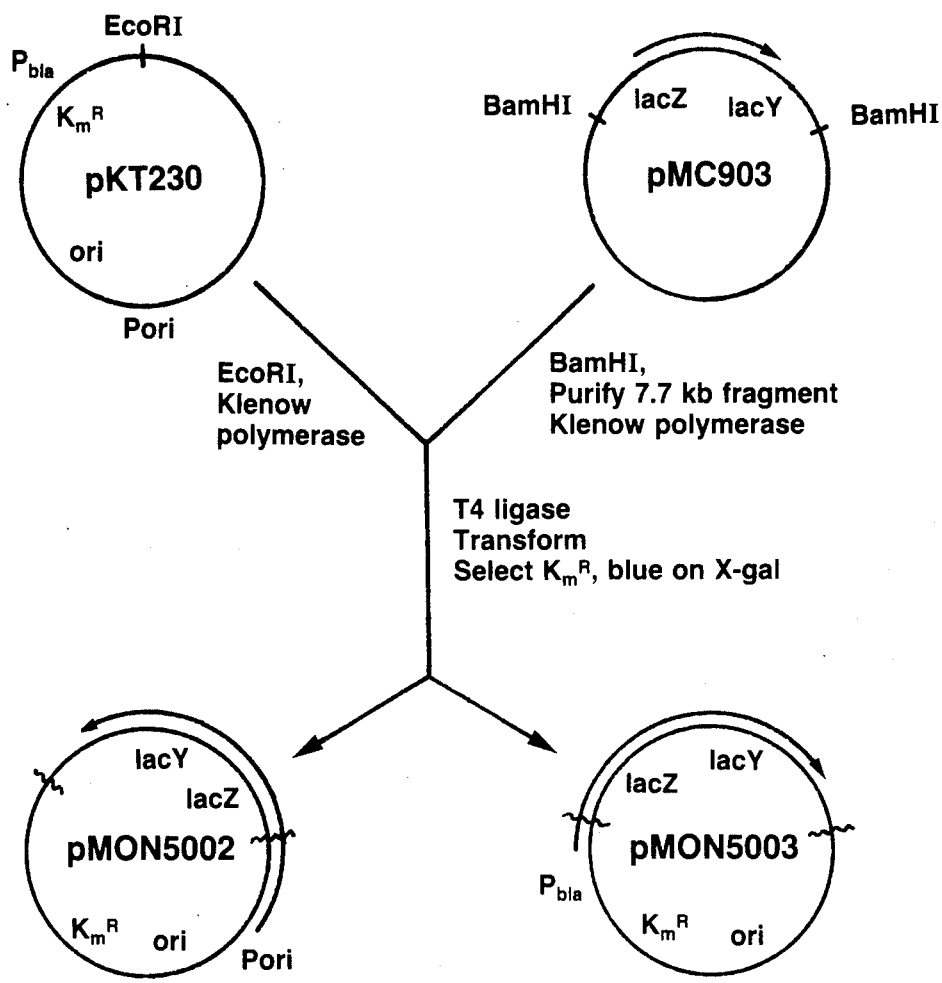
FIG. 1 depicts the creation of plasmids pMON5002 and pMON5003, which contain lacY and lacZ genes.

This invention is based upon a discovery that is contrary to the teachings of the prior art. This discovery resulted from the collection of a large number of bacterial isolates from soybean roots in four different states. Bacterial isolates were collected from those soybean roots and analyzed using a commercially available set of tests, referred to as the API20E tests. In addition to the API20E battery of tests, the bacterial isolates were also tested for fluorescence under ultraviolet light. An anomaly between the fluorescence test results and the API20E test results was observed for a cluster of isolates. This anomaly was investigated more carefully, and the subsequent investigation revealed that virtually all fluorescent pseudomonads might be deficient in the ability to hydrolyze ONPG, an indicator substance used to test for $\beta$-galactosidase (B-gal) activity. This finding was contrary to the teachings of Baumberg 1980, Hugh 1980 and Hemming 1982. Baumberg 1980 indicates that one species of fluorescent pseudomonad, out of two species tested, contained endogenous B-gal acitivity. Hugh 1980 indicates (in Table 6, p. 294) that strains from each fluorescent species tested (*Ps. aeruginosa, Ps. fluorescens* and *Ps. putida*) were capable of hydrolyzing ONPG and produced acid using lactose on purple agar base. Hemming 1982 indicated that 8 out of 176 fluorescent pseudomonads were capable of growing, on media containing lactose as the sole carbon source.

The anomaly between the fluorescent test results and the API20E test results led to additional, more careful testing of the fluorescent pseudomonad cultures which indicated ONPG activity. The additional tests revealed that cultures of ONPG-cleaving fluorescent pseudomonads had been contaminated with other bacteria that have ONPG activity, and that not a single fluorescent pseudomonad out of several hundred tested had true ONPG activity. These tests further revealed that no microorganisms, out of over 2,000 isolates tested, were capable of both (1) lactose utilization or ONPG cleavage, and (2) fluorescence on iron-deficient media at 398–498 nm when excited with ultraviolet light. Based on these discoveries, a program was commenced which involved transforming various fluorescent pseudomonad species with expressions vectors which contained one or more of the following lactose-related genes:

1. lacZ, a gene which encodes the beta-galactosidase (B-gal) enzyme. The B-gal enzyme cleaves lactose, a disaccharide sugar molecule, into two monosaccharide molecules (galactose and glucose) which can be utilized by most bacteria.

2. lacY, a gene which encodes for lactose permease, an enzyme which becomes embedded in the membrane of the host cell and actively transports lactose molecules into the cell.

3. lacI, a gene which encodes for a repressor protein which, in the absence of lactose, will bind to the promoter/operator region of the lac operon and thereby repress the expression of lacY and lacZ. If lactose is present in the cell, it will bind to the lacI protein, preventing it from repressing the expression of lacY and lacZ. The lacI$_q$ gene refers to a lacI gene with a promoter which causes abnormally high levels of expression of the lacI protein.

The plasmid construction program commenced with two plasmids which are described in the literature. Plasmid pKT230 (Bagdasarian 1981) will replicate in both *E. coli* cells and Pseudomonas spp. cells. It contains genes for resistance to kanamycin (Km$^r$) and streptomycin (Sm$^r$). Plasmid pMC903 (Casadaban 1980a) contains the lacZ and lacY genes on a promoterless 7.7 kilobase (kb) fragment bracketed by BamHI restriction sites. These two plasmids were used to construct pMON5002 and pMON5003, as described in Example 3. Both pMON plasmids contain intact lacY and lacZ genes, a Km$^r$ gene, and a pseudomonad-active origin of replication (ori). The construction and structure of these plasmids are depicted in FIG. 1. When these plasmids were used to transform various flourescent pseudomonad strains, they conferred upon those strains the following characteristics:

1. substantial growth capability on nutrient media containing lactose as the sole carbon source;

2. ability to hydrolyze at least two chromogenic substrates, ONPG and X-gal.

Two other plasmids, pMON5008 and pMON5012, were constructed which contain the lacZ (B-gal) gene but not the lacY (lactose permease) gene. When fluorescent pseudomonad strains were transformed with either of these plasmids, cell lysates were capable of hydrolyzing ONPG or X-gal. However, intact cells were capable of growing only very slowly (if at all) on medium containing lactose as the sole carbon source. Colonies containing pMON5008 or 5012 were blue on X-gal indicator plates, since X-gal (unlike lactose) is capable of entering *E. coli* and Pseudomonas spp. cells that are deficient in lacY.

The inability of viable cells transformed with lacZ to utilize lactose was unexpected. It indicated that the lacY gene was necessary to enable the transformed cells to ingest lactose. It also indicated that the lactose permease enzyme from *E. coli* is properly expressed in pseudomonads (which was expected) and then properly transported to and incorporated within the cell membrane, which was somewhat surprising in light of the fact that *E. coli* and pseudomonads belong not merely to different genera but also to different families of bacteria.

In an alternate preferred embodiment of the invention, several plasmids were constructed which caused fluorescent pseudomonads to express the lacY and lacZ genes inducibly. One such plasmid utilized the lac operon regulation system that is used by *E. coli*. This involved placing the lacZ gene under the control of the lac promoter/operator (P/O) sequence, and inserting into the expression vector a gene which encodes the lac repressor protein, lacI. In the absence of lactose inside the cell, the lacI protein binds to the P/O sequence, thereby preventing expression of the lacZ gene. However, if lactose molecules are present inside the cell, they will bind to the lacI protein, thereby preventing the lacI protein from binding to the P/O sequence. This allows for transcription and expression of the lacY and lacZ genes.

Plasmid pMC7 (Calos 1978) was digested with HincII to obtain a fragment which contains the lacI gene, the lac P/O sequence, and a small part of the lacZ gene. This lacI-P/O-lacZ sequence was inserted into pKT230 to create pMON5009, which contains both Km$^r$ and Sm$^r$ genes.

Plasmid pMON5009 was digested with PstI and PvuII, and the fragment containing the Sm$^r$ gene and most of the lacZ coding sequence was removed. The remaining fragment, which contained the lacI gene, the P/O sequence, and a very small (inactive) portion of the lacZ sequence, was ligated to pMON5012 which had been digested with PstI and SmaI. The resulting plasmid, pMON5015, contained the lacI gene and the P/O sequence, but it did not contain the lacY gene.

After the important role of the lacY gene in conferring lactose utilization capability upon pseudomonads was recognized, a lacY gene (obtained from pMON5003) was inserted into pMON5015 to create pMON5017, which has both lacY and lacZ under the control of the P/O sequence. pMON5017 was used to transform fluorescent pseudomonads. The results indicated that the lactose utilizing genes were inducible by IPTG, as described in Example 6.

To create a system that was both more inducible, and inducible by a totally independent means, the lacY and lacZ coding sequences were placed under the control of the aerobactin gene of *E. coli*, in a plasmid designated as pMON5022 (discussed in Example 7). The aerobactin promoter/operon (described in Stuart 1980) represses transcription in the presence of iron. This promoter/operon was selected because fluorescent pseudomonads are believed to have evolved a method for increasing the iron content within the cell cytoplasm. Briefly, the siderophore molecules of fluorescent pseudomonads are created within the cells, and exit the cells through the cell membranes. Once outside the cells, they chelate iron ions or molecules. The cell membranes contain receptor proteins which actively transport iron-bearing chelated siderophores into the cells, while nonchelated siderophores are not transported into the cells. As described in Example 7, plasmid pMON5022 (with the aerobactin promoter/operon) provided a higher degree of inducibility in pseudomonads than pMON5017 (with the lac promoter/operon).

Both pMON5017 and 5022 have a relatively low degree of repressibility; i.e., the lacY and lacZ genes are expressed at a relatively high level even in the absence of inducing conditions. The degree of repressibility can be increased if desired by various techniques known to those skilled in the art. As examples, alternate promoter systems can be utilized; transcription terminators may be inserted between the promoter and the coding sequence; competing promoters may be inserted to cause transcription in the opposing direction; and antibiotic resistance genes on the plasmid may be deleted or placed in an orientation that cannot cause read-through transcription. See Bagdasarian 1983. In addition, the desired genes may be inserted (e.g., by transposon mutagenesis) into the chromosomes of numerous bacteria, and bacteria having the insertion at preferred chromosomal locations may be selected.

If natural lactose-utilizing fluorescent pseudomonad bacteria are discovered in the future, it is extremely unlikely that they would have lacY or lacZ genes with the same induction characteristics of the inducible genes described herein. Therefore, by analyzing lacY or lacZ induction, it would be a simple matter to determine whether any lactose-utilizing bacteria was a naturally occurring strain or a descendant from an inoculated strain. In addition, the availability of different types of inducibility provides a means for inoculating more than one strain of transformed cell into a single location, and subsequently distinguishing between descendants of different inoculants.

In a laboratory setting, various transformed strains of fluorescent pseudomonads were inoculated onto soybean seeds which were planted in soil. The seeds germinated, and were allowed to grow until the tip of the main root reached the bottom of a tube fitted onto the bottom of the soil container. The roots were then harvested and assayed on nutrient media to determine the number of cells that descended from the inoculated bacteria. The results, described in Example 8, indicated that the transformed bacteria proliferated on the soybean roots, and that the inserted plasmids were sufficiently stable for tracking use despite the absence of any selective pressure during the seedling growth.

Similar experiments were conducted using non-sterilized soil in a growth chamber equipped with P2 containment facilities, defined by the Recombinant Advisory Committee of the National Institutes of Health. The preliminary results, described in Example 9, confirm the results of the laboratory experiments described above. The methods used in the growth chamber experiments are adaptable to field conditions by those skilled in the art.

All of the transforming plasmids described above contain genes which encode enzymes for resistance to the antibiotics kanamycin or streptomycin. Such genes are useful for plasmid manipulations in the laboratory. However, before a plasmid is used to transform a cell culture that is intended for environmental release, any undesired antibiotic resistance or other genes can be deleted from the plasmid or inactivated. A variety of methods to delete or inactivate such genes are known to those skilled in the art, such as full or partial digestion with one or more endonucleases to remove a DNA fragment containing part of the gene, followed by ligation of the remainder of the plasmid using oligonucleotide linkers if desired, followed by transformation of cells and growth on appropriate selective media (such as media containing lactose as the sole carbon source) to select a colony having the desired construct. For example, the $Sm^R$ gene described herein has three internal SphI cleavage sites, which can be used to inactivate that gene. The $Km^R$ gene contains internal XmaI, HindIII, and XhoI cleavage sites.

As used herein, "fluorescence" refers to fluorescence at a selected combination of excitation and emission wavelengths. For example, fluorescent pseudomonads emit light at 398–498 nm when excited by ultraviolet radiation at 290–390 nm. Such bacteria can be easily distinguished under ultraviolet light from other bacteria which fluoresce at different wavelengths. Therefore, the existence of microorganisms which fluoresce at some combination of wavelengths other than a selected combination will not impede tracking of microorganisms using the method of this invention.

This invention is not limited to use with soil bacteria. For example, as previously mentioned, certain species of fluorescent pseudomonads are human pathogens which are important in hospital and clinical settings. The marker genes of this invention will improve the ability of medical and veterinary scientists to track microoganisms in such environments. As used in the claims, the term "open environment" includes any medically or biologically significant location outside of a laboratory, fermentation vessel, or other location from which microorganisms have been deliberately excluded.

The term "selected environment" is used in a functional bounded sense. For example, if microbes are inoculated into an agricultural field, that field with its boundaries or possibly with the neighboring fields can be regarded as the selected environment for the purpose of tracking microorganisms. As another example, if microbes are inoculated into a fermentation or hydroponic vessel, the inoculated vessel, its contents and any piping or vessels connected to it may be regarded as the selected environment.

As used herein, the term "inoculate" includes any deliberate introduction of genetically transformed microorganisms into a selected environment. For example, microorganisms could be inoculated into a field of soil by spraying, injection, planting of seeds that have been contacted with the microbes, etc. Inoculation may introduce microbes into one or more specific locations in an environment, or it may disperse microorganisms throughout the environment. Inoculate does not include passive, accidental, or other unintended introductions of microorganisms.

The marker genes of this invention may be used with numerous species of fluorescent pseudomonads which are publicly available (see, e. g., pages 167-181 of the catalog (15th edition,1982) of the American Type Culture Collection (Rockville, Md.). However, these genes are not limited to use with bacteria of the genus Pseudomonas. For example, several other genera of bacteria, including Proteus, are believed to be composed predominantly of species which are incapable of utilizing lactose, with subpopulations capable of utilizing lactose. Such lactose-utilizing subpopulations may be erroneously identified contaminated cultures, similar to the contaminated pseudomonad cultures discussed previously. Using the information provided herein, bacteria within such genera may be re-evaluated more carefully to determine whether they are truly capable of utilizing lactose. If not, lactose-related genes may be used with such bacteria according to the method of this invention.

In addition to tracking bacteria, the method of this invention may be used to track other types of microorganisms, such as yeast and other fungi. Many fungi are known to be deficient in $\beta$-gal activity, and using screening procedures known to those skilled in the art, it is possible to identify combinations of phenotypic traits which do not exist in naturally occurring fungi or other microorganisms. A method of transforming fungi was reported in Dhawale 1984.

In addition to the lac genes discussed herein, other genes which do not involve antibiotic resistance may be suitable marker genes for tracking microorganisms in open environments. One such gene, designated the xylE gene, encodes the enzyme catechol dioxygenase. Some species of pseudomonad bacteria carry the xylE gene on a plasmid which is commonly designated the TOL plasmid, which enables the host cells to degrade toluene; see Zukowski 1983. When colonies of bacteria which contain catechol dioxygenase are sprayed with catechol, they turn yellow. This may allow the xylE gene to serve as a chromogenic marker. If it is used in conjunction with a second phenotypic trait that does not coexist within cells that contain catechol dioxygenase activity, it may be used to track microorganisms using the method of this invention. Suitable second phenotypic traits may be determined using screening procedures known to those skilled in the art.

The tracking method of this invention may be confirmed or supplemented by any other method of microbial analysis if desired. For example, if a combination of two phenotypic traits indicates that a colony of cells descended from a culture of inoculated cells, additional analyses (such as DNA probes) may be used to confirm that indication if desired.

The marker genes of this invention can also be used to track various other genes or transposons which are not easily assayable. This capability is important in analyzing the transfer of DNA between different bacteria. By placing a selected marker gene of this invention in proximity to another gene of interest (typically on a plasmid or transposon; alternately on a chromosome, if desired), it is possible to determine whether the segment of DNA containing both genes has been transferred from one strain of bacteria to another strain.

If desired, a combination of three or more phenotypic traits (including one, two, or more genetically transformed traits) may be used to track microorganisms. For example, a cell culture which is fluorescent and has both B-gal and catechol dioxygenase activity could be inoculated into a selected enviroment, and cells could be sampled after a selected period of time. The presence of all three traits in a cell sample from the inoculated environment would indicate that the cells in the sample descended from the inoculated cells.

The genetically transformed microbial culture of this invention may be mixed with other materials to facilitate their inoculation into an environment. For example, microbes used for soil inoculation can be sprayed or coated (in liquid form) or otherwise contacted with plant seeds. The plant seeds can then be dried or otherwise processed for subsequent handling and planting. Alternately, a microbial culture of this invention can be contacted with roots and allowed to proliferate, and the roots can be harvested, divided into a convenient particle size, and used. As another alternative, microbes for soil inoculation can be mixed or otherwise contacted with soil, sand, vermiculite, fertilizer, herbicide formulations, or other matter that is suitable for distribution upon an agricultural field. Any such matter (seeds, roots, soil, etc.) which is intended to facilitate environmental distribution is referred to in the claims as "carrier material."

Those skilled in the art will recognize, or may ascertain using no more than routine experimentation, numerous equivalents to the specific embodiments described herein. Such equivalents are within the scope of this invention.

EXAMPLES

Example 1: Bacterial Characterization and Cluster Analysis

A collection of 2,045 bacterial isolates was assembled from 8 locations in 4 states as follows. Rootballs containing soil and roots of soybean (*Glycine max* (L.) Merr. cv. "Williams") plants at various stages of maturity were harvested. Soil was shaken off of the roots, and the roots were rinsed with distilled water and weighed. Each root was then treated using one of three different methods; all three methods were used in order to maximize the number of isolates gathered. The first method involved removing all lateral roots from a main root, placing the lateral roots from one plant in sterile water at room tem-perature and shaking the water for 1 hour. The main root was placed in water and shaken separately. The second method involved dividing a root into top, middle, and bottom segments. Each segment (lateral roots and part of the main root) was shaken in water as above. The third method involved combining 15 to 30 roots and homogenizing them in sterile water.

After treatment using one of these methods, the water or homogenate was serially diluted. Each of several dilutions were plated onto seven different bacterial growth media. Media which were mixed before use included nutrient broth yeast extract (Vidaver 1967), BCBRVB medium (Sands 1980), King's B medium (King 1954), and azospirillum isolation agar (Becking 1981) Purchased media included MacConkey medium, potato dextrose agar supplemented with 2% proteose peptone #3, and pseudomonas F agar all sold by Difco Laboratories, Detroit, Mich.

Numerous colonies were selected, given arbitrary designations, and subcultured two or three times for purity before performance and recording of the Gram reaction and placement into storage. Extended subculture was restricted to avoid "attenuation" phenomena (e.g., loss of possible plant pathogenicity or plant recognition characters, loss of plasmid-borne traits, etc.). Preservation of isolates was performed by the addition of an equal volume of 30% glycerol to the nutrient broth culture of the subcultured bacterium with subsequent storage at −70° C. Incubation temperatures were generally about 27° C.

A subset of the collection was subjected to a battery of phenotypic tests provided in commercial kits (API20E tests) following the instructions of the kit supplier (Analytab Products Inc., Plainview, N.Y.). The ONPG test in the API20E battery uses intact, viable cells.

Results of the API20E phenotypic tests were coded in binary fashion (1 for positive and 0 for negative) prior to systematic numerical analysis. Numerical analysis was then performed on these nonidentified isolates along with known reference strains which also had been simultaneously characterized using the same phenotypic tests. Similar numerical analyses have been described in, e.g., Atlas 1981, Sneath 1973, and Griffiths 1980.

A computer program, EDITMAT (Walczak 1980; a gift from M. Krichevsky, Microbial Systematics Section, National Institute of Dental Research, NIH, Bethesda, Md.), was used to edit the matrix of binary data and to provide basic information about the data prior to cluster analysis. A matrix of 577 bacterial isolates having complete data for 24 of the API20E tests was assembled using EDITMAT and subjected to cluster analyses using both the simple matching coefficient S(sm) (Sokal 1958) which includes both positive and negative similarities, and the similarity coefficient S(j) of Jaccard (Sneath 1957) which excludes negative matches. Sorted similarity matrices and dendrograms of strain similarities were obtained by unweighted average linkage clustering (Sneath 1973). Ward's method of analysis was computed from the distance matrix (Wishart 1978).

In addition, these isolates were plated onto King's medium B (King 1954) and examined after 24 and 48 hrs of growth for diffusable fluorescent pigment production detectable under long U.V. irradiation 366 nm). The fluorescent test data was compared to the cluster data described above. The comparison indicated that about 10% of the fluorescent isolates were found in a cluster of 80 members possessing characteristics identifiable with strains of the family Enterobacteriaceae, a bacterial family that excludes pseudomonads. This anomaly was further investigated.

The fluorescent members of the anomalous cluster had also tested positive for the presence of B-gal activity, as indicated by ONPG cleavage in the API20E test battery. Since none of the fluorescent isolates of the other clusters presented this phenotype, each fluorescent isolate of cluster 6 was carefully examined for purity. All fluorescent isolates which initially tested positive for ONPG activity were found to be contaminated cultures. In all cases, the ONPG hydrolysis activity was attributable to a nonhydrolysis fluorescent contaminating member of the mixed culture identified as a member of the Enterobacteriaceae rather than from the fluorescence-producing member of the mixed culture was a pseudomonad.

The unexpected results indicated by the anomalous fluorescent cluster, followed by more cautious analysis of its true chracteristics and recognition of the contaminating strains, led to the realization that virtually all fluorescent pseudomonads might be deficient in ONPG hydrolysis activity. To assess that possibility, over 430 fluorescent pseudomonad isolates were carefully tested as described in Example 2. The 430 fluorescent pseudomonad isolates were the only microorganisms out of over 2,000 isolates tested that emitted light at 398–498 nm when excited by ultraviolet light after growth on iron-deficient media. Therefore, not a single strain of bacteria, out of over 2,000 isolates tested, was capable of both significant ONPG hydrolysis and fluoresence as described.

Example 2: Growth Tests of Wild Type Isolates on Lactose

Fluorescent isolates were tested for significant 3-day growth on M9 minimal salts medium (Miller 1972) containing 1% lactose as the sole carbon source. Single colonies of each wild type isolate were transferred to a master plate in preparation for replica plating. The master plate medium consisted per liter of the following: yeast extract (1.0 g), glycerol (3.0 ml), $Na_2HPO_4$ (4.2 g), $KH_2PO_4$ (2.7 g) and agar (15 g). A total of 430 test isolates, with at most 10 different test colonies per plate, were replicated from master plates onto solid-agar plates of lactose M9 minimal salts medium using a "Cathra" multipoint replication system (Diagnostic Equipment Inc., St. Paul, Minn.). After incubation for 4 days at 27° C, the plates were examined for growth in comparison to control plates. All but four isolates failed to produce significant growth on this medium. The four cultures capable of growth on lactose were replicated onto King's medium B plates, and on M9 lactose plates; 40 ul of 4% X-Gal in dimethyl formamide had been spread on the surface of each plate. Following similar incubation, all four colonies exhibited a light blue coloration on the lactose medium (which results from hydrolysis of the X-gal by beta-galactosidase or similar activity) and also were found to exhibit fluorescence on King's medium B. These four growth-positive colonies were streaked for isolation. It was possible to discern, by differences in colony morphology and subsequent repeated API20E testing, that three of the original colonies represented mixed cultures where the ability of a non-fluorescent contaminant strain to hydrolyze lactose to galactose and glucose had provided carbon substrate enabling growth of a fluorescent pseudomonad. The fourth original colony was not detected as being a mixed culture. Its growth was relatively poor on this medium and its coloration was a very light blue indicating only slight X-gal hydrolysis.

Example 3: Creation of pMON5002 and pMON5003 with lacE and lacY Genes

Five ug of plasmid pKT230 (with kanamycin and streptomycin resistance genes, designated as $Km^r$ and $Sm^r$; described in Bagdasarian 1981; gift of M. Bagdasarian, Max Planck Inst., FRG) were purified from *E.* coli C600galK- host cells by alkaline-SDS extraction and NACS-52 resin column chromotography (obtained from Bethesda Research Laboratories, Bethesda, Md., and used as per manufacturer's instructions). The DNA was digested with 15 units of EcoRI (all restriction endonucleases were obtained from New England Biolabs, Beverly, Mass., and were used with buffers according to the supplier's instructions, unless otherwise specified) for 1 hour at 37° C. Following ethanol precipitation (Maniatis 1982), the restricted DNA was treated with 25 units E. coli DNA polymerase (Klenow fragment; New England Nuclear Corp., Boston, Mass.) and 50 μM of each dNTP at 37° C. for 2 hours to fill in staggered ends.

Plasmid pMC903 (with lacY and lacZ genes; described in Casadaban 1980a; a gift of M. Casadaban, U. of Chicago) was purified as described for pKT230 from E. coli HB101 cells, and 12 μg were digested with 20 units BamHI at 37° C. for 1 hour. After digestion, the DNA fragments were separated by electrophoresis on a 0.7% agarose gel in Tris-acetate buffer (40 mM Tris base, 20 mM sodium acetate, 1 mM EDTA, 15 ml/l glacial acetic acid, pH8) and visualized by UV fluorescence after ethidium bromide staining. The 7.7 kb fragment which contains lacZ and lacY was cut from the gel and purified by adherence to Adsorbsil-5 silica beads (Altex Co., Ann Arbor, Mich.). For this, a 3 cm×3 mm×3 mm section containing the 7.7 kb DNA fragment was cut from the gel, sliced into 3 mm cubes and placed in a 1.5 ml Eppendorf tube. This was filled to within 100 μl of the top with 8M sodium perchlorate, and mixed by inversion until the gel pieces dissolved (10 min). Approximately 1 mg of Adsorbsil-5 resin was added, and the tube was mixed by inversion for 20 min. The DNA-containing resin was collected by centrifugation for 2 min, washed with 1 ml each of 6M sodium perchlorate and ethanol, and dried under vacuum for 4 min. 90% of the DNA was recovered by resuspending the resin in 30 μl of 10 mM Tris-HCl (pH 7.5) buffer and incubation for 15 min at 37° C. The DNA was then treated with DNA polymerase (Klenow fragment) to fill in staggered ends, and ethanol precipitated.

Approximately 3 μg of the purified 7.7 kb fragment was mixed with the EcoRI restricted/blunt-ended pKT230 DNA, along with 10 units of T4 DNA ligase (prepared by the method of Murray 1979) and 400 μM ATP (one unit of T4 DNA ligase will give 90% circularization of one μg HindIII-cleaved pBR327 plasmid in 5 min at 22° C.). This mixture was incubated for 14 hours at 16° C., at which time the ligated DNA was used to transform CaCl₂-shocked E. coli JM101 lac- cells (Maniatis 1982). After expression in Luria broth (LB) for 1 hour at 37° C., the cells were spread on solid LB media plates containing 50 μg/ml kanamycin, and which had been overspread with 40 μl per plate of 4% X-Gal in dimethyl formamide. Following incubation for 16 hours at 37° C. several thousand colonies appeared. Approximately 40% of these were dark blue, indicating successful insertion and expression of the lacZ gene (and, as was later discovered, the lacY gene) in the vector plasmid. Plasmid mini-prep DNA was prepared from 8 blue and 4 white colonies (Ish-Horowicz 1981). HaeIII endonuclease digestion and analysis by 5% polyacrylamide gel electrophoresis verified that plasmids from the blue colonies all carried the 7.7kb insert fragment. One plasmid in which the fragment had been inserted in a counter-clockwise orientation (all arrows on figures point in the 5' to 3' direction on the mRNA) was designated pMON5002; another with the fragment in a clockwise direction was designated pMON5003, as indicated in FIG. 1. Since the cloned 7.7 kb fragment does not contain a transcriptional promoter upstream of lacZ gene, expression in the constructed plasmids is from promoters contained on the pKT230 vector. On pMON5002, the promoter causing lacZ transcription is believed to be near the origin of replication based on RNA polymerase binding studies (Bagdasarian 1981); this promoter is designate $P_{ori}$. On pMON5003, expression is believed to be caused primarily by the $P_{bla}$ promoter.

Example 4: Creation of pMON5008 And pMON5012 With lacZ, Without lacY

To eliminate the lacY gene and simultaneously create a new HindIII site that would permit future C-terminal fusions of desired proteins with the entire β-galactosidase molecule, four oligonucleotides were synthesized (by the method of Adams 1983) having the following sequences:

(1)     5'-CCAGTTGGTCTGGTGTCAAAAATAAGCTTA- 3'
(2)     -AATTCCAGCTGAGCGCCGGTCGCTACCATTA-
(3)     -CTGGTAATGGTAGCGACCGGCGCTCAGCTGG-
(4)     -GATCTAAGCTTATTTTTGACACCAGACCAA-

Figure 2:
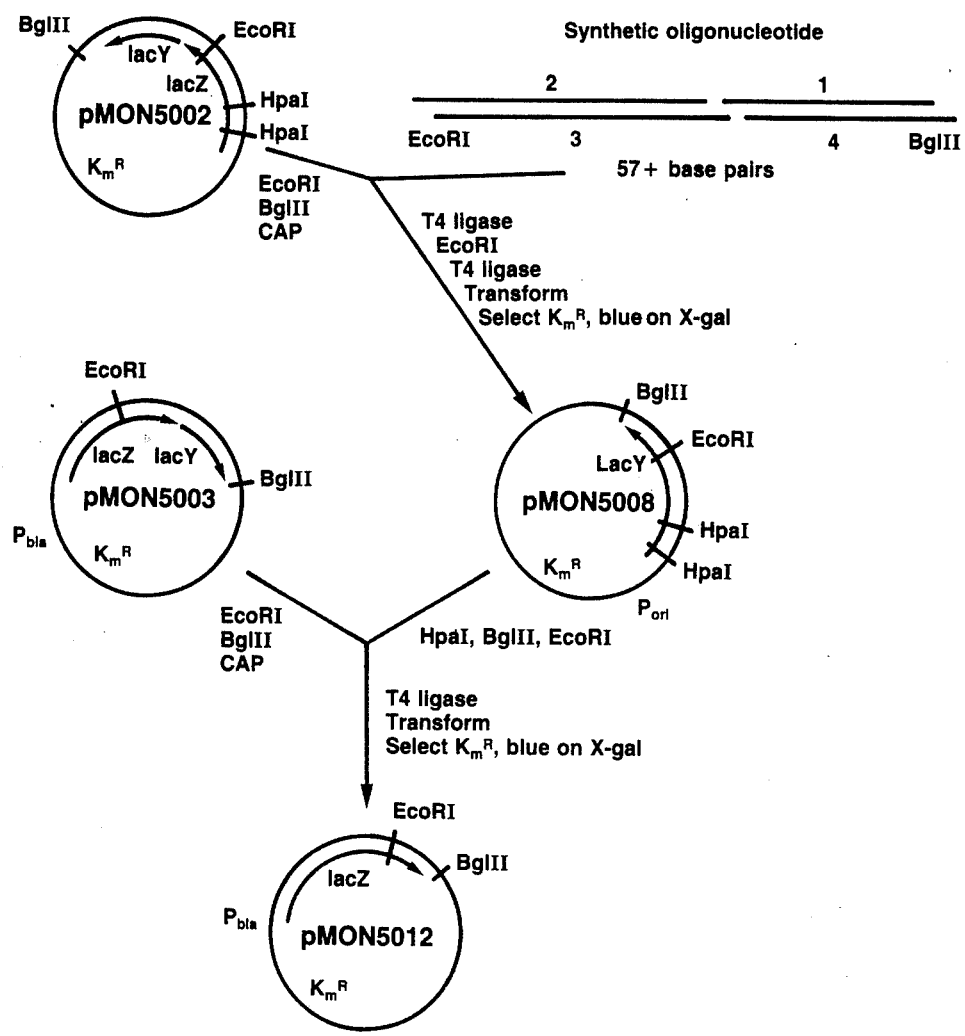
FIG. 2 depicts the creation of pMON5008 and pMON5012, which contain the lacZ but not the lacY gene.

These oligonucleotides were treated with polynucleotide kinase and 400 μM ATP to phosphorylate the 5' terminal residues, and 2 pmoles of each were combined in a 50 μl volume. After addition of 20 units of T4 DNA ligase and 1 mM ATP, the mixture was incubated at 4° C. for 48 hours. As indicated in FIG. 2, the oligonucleotides annealed and ligated to each other to form a 57 bp double stranded DNA with single stranded EcoRI and BglII overhangs.

Separately, 5 μg of plasmid pMON5002 (described in Example 3) were digested with BglII, ethanol precipitated, and restricted again with EcoRI. This deleted a fragment containing the entire lacY sequence and a small portion of the lacZ sequence. The remaining portion of pMON5002 was then combined with a four fold molar excess of the 57+ bp synthetic oligonucleotide, 1 mM ATP and 10 units of T4 DNA ligase. Insertion of the 57+ sequence replaced the small portion of the lacZ sequence which had been deleted during the pMON5002 digestion. After incubation at 16° C. for 18 hours the DNA was re-digested with EcoRI and re-ligated to eliminate multiple synthetic oligonucleotide inserts. The resulting DNA mixture used to transform CaCl₂-shocked E. coli JM101 lac- cells, which were plated on LB media plates containing kanamycin and X-Gal, as described in Example 3. Approximately 300 blue colonies were selected. Plasmid mini-prep DNA was prepared from 10 of these, and 5 were found to contain the synthetic oligonucleotide replacement after analysis by BamHI and EcoRI digestion and agarose gel electrophoresis. The plasmid contained in these colonies was designated as pMON5008, as indicated in FIG. 2.

To create pMON5012, 7 μg of plasmids pMON5008 and pMON5003 were separately digested with BglII and EcoRI. One unit of calf-intestine alkaline phosphatase (CAP; Beohringer-Mannheim, Indianapolis, Ind.) was added to the digested pMON5003, and allowed to react for 15 min at 37° C. Restricted pMON5008 was digested with 10 units of a third enzyme, HpaI which inactivated its lacZ gene. The resulting MON5008 DNA was combined with the restricted, CAP treated pMON5003 DNA, 20 units T4 DNA ligase, and 500 μM ATP. The mixture was incubated 16 hours at 16° C., and used to transform CaCl$_2$-shocked E. coli M182 (Δlac) cells. Blue colonies obtained on LB/kanamycin/X-Gal plates were verified (by restriction analysis using BglII, BamHI, and HindIII) to confirm that they carry the synthetic oligonucleotide in the opposite orientation to pMON5008. One of these plasmids was designated pMON5012.

Example 5: Analysis of Transformed Fluorescent Pseudomonads

Plasmids pMON5002, 5003, 5008, and 5012 (as well as pKT230, used as a control) were moved from their original E. coli hosts into various rifampicin resistant (rif-R) fluorescent pseudomonads described in Example 1 via a tri-parental mating system. This procedure utilizes helper plasmid pRK2013, which provides the gene products necessary to mobilize the pKT230 and pMON plasmids for mating into various gram negative bacteria, but which is itself incapable of replication in Pseudomonas (Figurski 1979).

Five ml broth cultures of E. coli HB101 (pRK2013), Ps. fluorescens 701El rif-R, and the E. coli strains carrying pMON5002, pMON5003, pMON5008, pMON5012, or pKT230, were prepared in LB medium containing 50 μg/ml kanamycin (for E. coli cells) or 50 μg/ml rifampicin (Pseudomonas cells). These were shaken overnight at 30° C. For each mating one ml of each culture was centrifuged for 2 min, washed in 1 ml LB broth without antibiotics, re-spun, and resuspended in 33 μl of LB. The three cell suspensions (e.g., E. coli HB101(pRK2013), Ps. fluorescens 701Elrif-R, and E. coli JM101(pMON5002)) were combined, spotted onto the center of an LB plate, and incubated at 30° C. for 14 hours. Cells were then resuspended from the plate in 2 ml 10 mM MgSO$_2$, and dilutions were replated onto solid King's medium B (Pseudomonas agar F; Difco Laboratories, Detroit, Mich.) containing 50 μg/ml each of kanamycin and rifampicin, and 0.0025% X-Gal. After incubation at 30° C. for 48 hours, colonies arising were blue and fluorescent, and found to be the Pseudomonas host harboring only the appropriate pMON plasmid. To compare B-gal production from the transformed pseudomonas strains with that of E. coli, all plasmids were first moved into another E. coli derivative M182 (Casadaban 1980b) which has a more extensive deletion of the host lac operon. This results in lower background levels of endogenous B-galactosidase activity and eliminates any alpha complementation (Miller 1978) which may occur in E. coli JM 101. For this, one μg of each plasmid was mixed with CaCl$_2$-shocked E. coli M182 cells, and transformants were selected on appropriate media containing 50 μg/ml each of kanamycin and rifampicin. B-gal levels were then measured by cleavage of ONPG results of these assays are listed in Table I. B-gal activity is expressed in the standard units described in Miller 1972.

TABLE I

| β-galactosidase Assays from Various Transformed Bacteria (units: Miller 1972) | | |
|---|---|---|
| Plasmid | E. coli M182 | Ps. fluorescens 701E1 |
| none | <1 | <1 |
| pKT230 | <1 | <1 |
| pMON5002 | 330 | 10,200 |
| pMON5003 | 8,039 | 14,881 |
| pMON5008 | 130 | 2,082 |
| pMON5012 | 3,107 | 6,584 |

Figure 3:
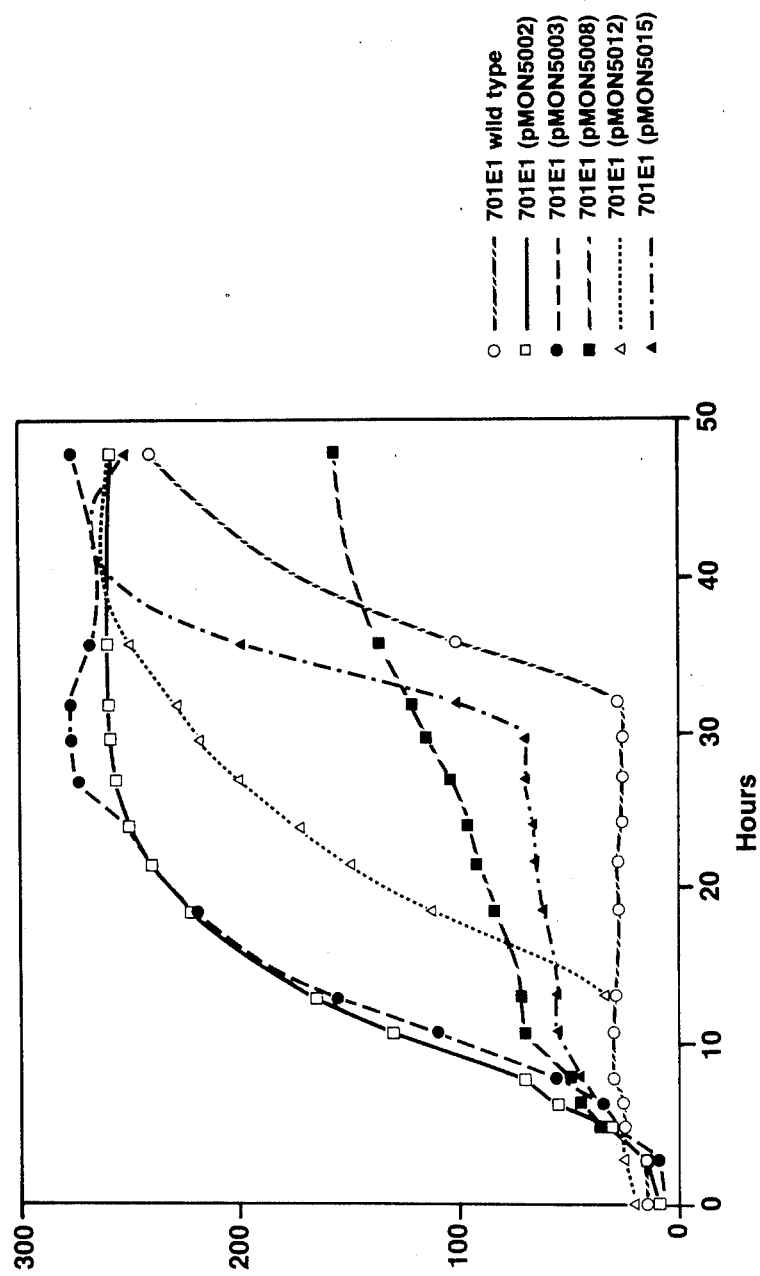
FIG. 3 depicts the ability of fluorescent pseudomonad strain 701E1, transformed by various pMON plasmids to grow on media containing lactose as a sole carbon source.

To assess the ability of transformed Ps. fluorescens strain 701El to utilize lactose as a sole carbon source cultures containing various plasmids were grown to saturation overnight at 30° C. in LB medium. These were subcultured to 25 klett units in 50 ml M9 minimal salts medium containing 1% lactose and shaken continuously at 30° C. Growth was monitored by OD$_{565}$ readings, indicated as klett units in FIG. 3. The arrow indicates the time at which 1% glucose was added to the media to verify cell viability.

Four other fluorescent pseudomonad strains (designated as 1894D3, 295D1, 1781E2, and 1141F1) which are incapable of significant growth on lactose M9 minimal salts medium were individually transformed with pMON5002 or 5003. Each strain was cultured overnight in 4 ml LB at 28° C., and subcultured in 50 ml LB until it grew to an optical density of 25 klett units. A culture was grown with shaking at 30° C. to 110 klett units, at which time the culture was chilled on ice 10 min. Cells were centrifuged at 5,000 rm for 5 min in a Beckman JA-17 (or JA-21) rotor, and resuspended in 25 ml ice cold 150 mM MgCl$_2$ in 10 mM Tris-HCl (pH 8.0). After 20 min incubation on ice, cells were again pelleted and resuspended in 1.0 ml 150 m, MgCl$_2$/Tris. These remained on ice 1–3 hours prior to transformation. Alternatively, cells could be mixed with 20% glycerol and stored indefinitely at −80° C. with a one log loss in transformation efficiency.

100–200 μl of cells were transformed by mixing gently with 10–20 μl of pMON5003 DNA, and incubating 10 min on ice, 3 min at 42° C., and 10 min again on ice. The mixture was then added to 1-2 ml LB broth, and incubated with shaking at 30° C. for 1 hour. Aliquots were then plated on appropriate selection media, and incubated 48 hours at 28–30° C.

All four strains gave rise to transformants which were capable of significant growth on lactose M9 minimal salts solid-agar medium when transformed with pMON5002 or 5003. However, the wild-type strains and strains containing the vector pKT230 were not.

Example 6: Creation of pMON5009, 5015, And 5017

To create pMON5009, five μg of plasmid pMC7 (Calos 1978; gift of A. Summers, U. of Georgia) were partially digested with 2 units of HincII for 15 minutes at 37° C., and the 1724 bp fragment was isolated on a 5% polyacrylamide gel carried out in Tris-borate buffer, as described by Bolivar 1977. The fragment was then cut from the ethidium bromide-stained gel and extracted by electroelution (Allet 1973). This fragment carries the lactose promoter/operator region (P/O) and a gene designated as lacI$^q$ which encodes the lactose operon repressor protein I. Approximately 0.7 μg of this fragment was mixed with 5 μg of pKT230 which had been digested with BamHI and HpaI, and treated with E. coli DNA polymerase (Klenow fragment) to fill in the staggered BamHI ends, then T4 DNA ligase. E. coli JM101 cells were then transformed with this DNA and selected on LB plates containing 50 μg/ml kanamycin and overspread with 4% X-Gal in methyl formamide and 40 μl of 100 mM IPTG. Since the resulting plasmid contains 439 bp of the lacZ gene, an N-terminal segment of β-galactosidase is produced which is capable of alpha complementation in *E. coli* JM101 (see Zabin 1978), thereby providing a means for selection of clones carrying the 1724 bp segment. Positive candidates were verified by restriction analysis, using BamHI, EcoRI, HindIII and HpaI, and one of these was designated pMON5009.

To create pMON5015, five μg of pMON5009 were digested with PstI and SmaI, and combined with five μg of pMON5012 which had been cut with PstI and PvuII. This was treated with 2 units of T4 DNA polymerase and 50 μM of each dNTP to create flush ends on all fragments, and treated with T4 DNA ligase and 500 μM ATP. Competent *E. coli* M182 cells were then transformed and selected on LB plates containing kanamycin, X-Gal, and IPTG. Plasmids from blue colonies were examined for the presence of an EcoRI site and loss of the PstI site to identify the expected construct, which was designated pMON5015.

To create pMON5017, four μg of pMON5015 were digested with EcoRI and BglII, and treated with CAP. Six μg of pMON5003 were restricted with BglII and EcoRI, and approximately 0.8 μg of the 3.7 kb fragment which carries the lacY gene were isolated via Adsorbsil-5 resin binding. This was combined with the restricted pMON5015, T4 DNA ligase, and 500 μM ATP, incubated at 16° C. for 14 hours, and used to transform CaCl$_2$-shocked *E. coli* M182 cells. Transformants were selected as blue colonies on LB plates containing kanamycin, X-Gal, and IPTG, and plasmid DNA from final candidates was analysed on agarose gels after restriction with EcoRI and BglII. A plasmid with the desired structure was designated pMON5017.

Figure 4:
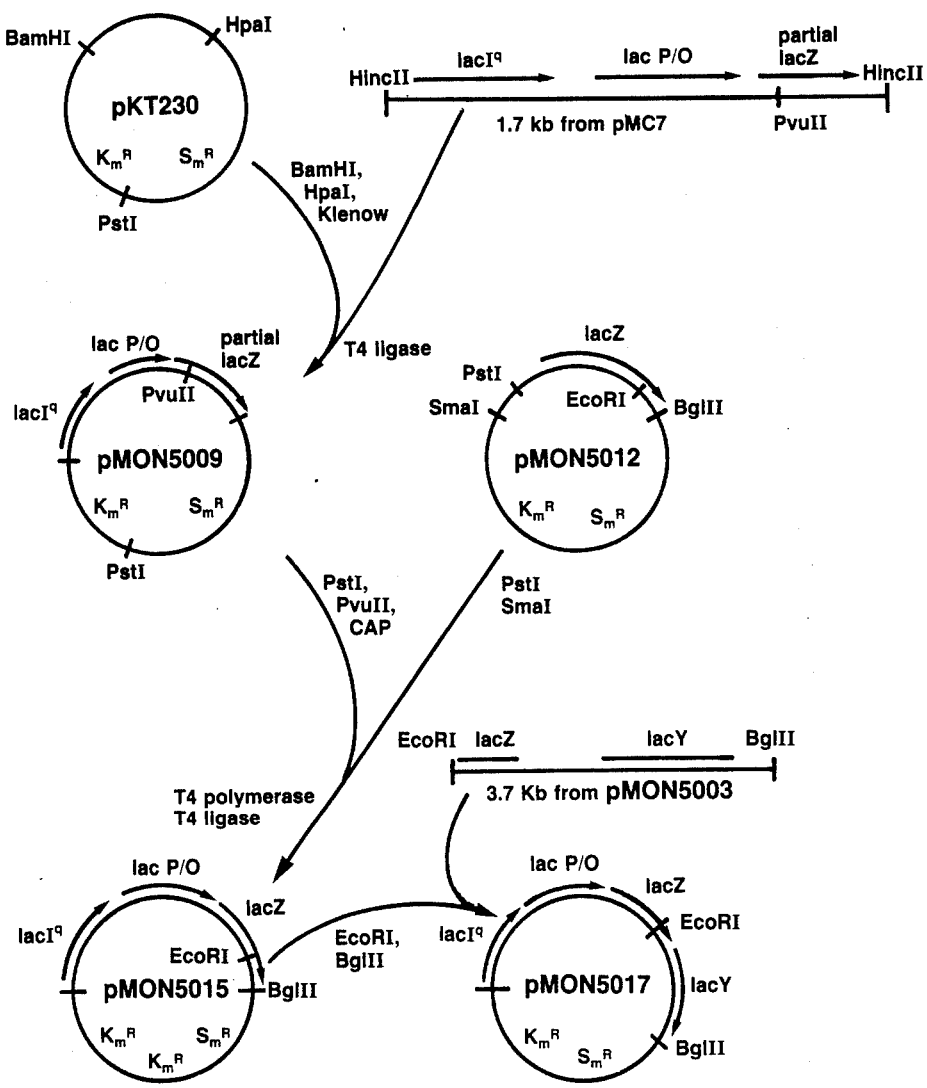
FIG. 4 depicts the creation of pMON5015 (lacZ) and pMON5017 (lacZ and lacY) under the control of the lac P/O operon and the lacI repressor gene.

The construction of pMON5009, 5015, and 5017 is depicted in FIG. 4.

To assess the level of transcriptional control in Pseudomonas mediated by the lacI repressor, pMON5017 was introduced into Ps.fluorescens 701EIrif-R via the tri-parental mating procedure described in Example 5. The resultant production of β-galactosidase in these transformed cells with or without the inducer IPTG (0.2 mM), as well as that from the *E. coli* host carrying pMON5017, was assayed by ONPG cleavage. The results, in Table II, are expressed in the units of Miller 1972.

TABLE II

| | Induction of β-galactosidase with IPTG | |
|---|---|---|
| Plasmid | E. coli M182 | Ps. fluorescens 701E1 |
| pMON5017 − IPTG | 11,209 | 18,688 ± 50 |
| pMON5017 + IPTG | 12,466 | 22,234 ± 50 |

Example 7: Creation of pMON5013, 5019, And 5022

Figure 5:
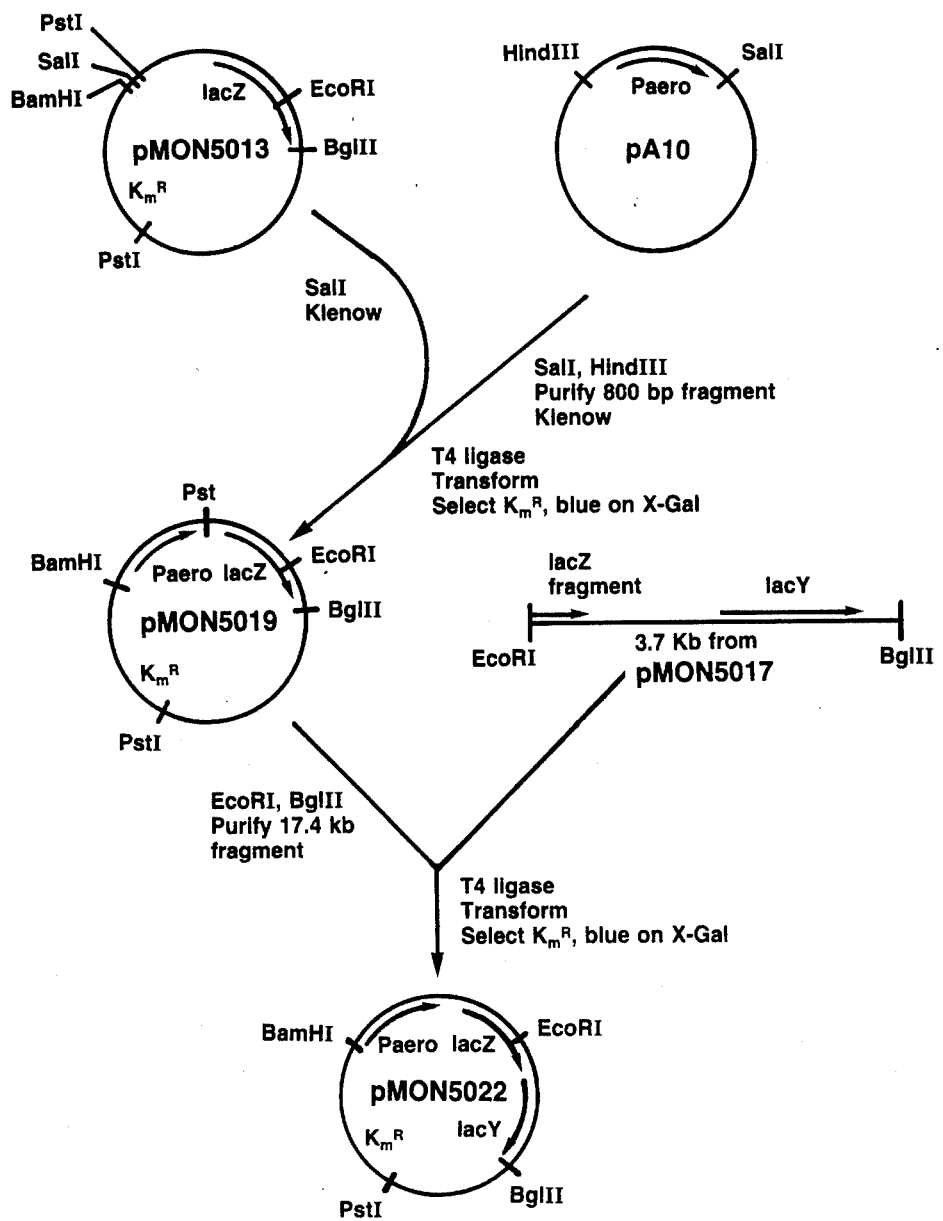
FIG. 5 depicts the creation of pMON5022, which has the lacY and lacZ genes under the control of the aerobactin promoter, which is repressed by iron.

To create plasmid pMON5013, seven μg of pUC18 (gift of J. Messing, U. of Minnesota) were digested with HaeII, PstI, and BamHI to obtain a short oligonucleotide containing BamHI and PstI ends and a SalI cleavage site. This oligonucleotide was combined with five μg of pMON5012 (which carries the lacZ gene but not lacY) which had been digested with PstI and BamHI. This was reacted with T4 DNA ligase and 500 μM ATP and used to transform *E. coli* JM101. Transformed cells were selected on LB plates with 50 μg/ml kanamycin, 0.002% X-Gal. Plasmid DNA from colonies which were white after 16 hours incubation at 37° C. was prepared and tested for correct assembly by agarose gel restriction pattern analysis after digestion with SalI, BamHI, PstI, and EcoRI. One positive candidate was designated pMON5013. This plasmid, shown in FIG. 5, contained two unique restriction sites (BamHI and SalI), and it did not contain the P$_{bla}$ promoter of pMON5012.

Next, the promoter region from the *E. coli* aerobactin operon (P$_{aero}$; Stuart 1980) was inserted upstream of the lacZ gene on pMON5013 to create pMON5019. For this, five μg of pMON5013 were digested with SalI and treated with *E. coli* DNA polymerase (Klenow fragment). This was combined with 10 μg of plasmid pA10 (similar to pABNS described in Bindereif 1983; gift of A. Bagg, U. of Calif.) which had been restricted with SalI and HindIII and also treated with DNA polymerase (Klenow fragment). T4 DNA ligase and 500 μM ATP were added to this mixture, which was incubated at 16° C. for 18 hours, and used to transform *E. coli* JM101 as before. Transformants were selected as blue colonies on M9 minimal salts solid media plates supplemented with 50 μg/ml kanamycin, 0.4% glucose, and 0.002% X-Gal. Plasmid DNA from these were tested by analysis of gel restriction patterns after digestion with BamHI and PstI, and one of the positive candidates was designated pMON5019, shown in FIG. 5.

The lacY gene was then added to pMON5019 to create pMON5022. For this, 5 μg of pMON5019 and 5 μg pMON5017 were both digested with BglII and EcoRI. The 3.7 kb fragment from pMON5017 and the 17.4 kb fragment from pMON5019 were purified via adsorption to DEAE membrane strips (SNS NA-45; Schleicher and Schuell, Inc., Keene, N.H.; used as per manufacturer's instructions). These fragments were then combined with T4 DNA ligase, incubated as before, and used to transform *E. coli* JM101. Colonies arising on LB plates containing 50 μg/ml kanamycin and 0.002% X-Gal were tested by EcoRI, BglII, and HindIII digestion of plasmid DNA to verify the addition of the lacY containing fragment. One of the positive candidates was designated pMON5022, shown in FIG. 5.

To test the degree of iron-regulated lacY expression in Pseudomonas, pMON5022 was moved into *Ps. fluorescens* 701EIrif-R by the tri-parental mating system described above. β-galactosidase levels in 701E1 with pMON5022 and in *E. coli* JM101 with this plasmid (Table III) were assayed by ONPG cleavage in M9 minimal media supplemented with 0.4% glucose and 20 μM ferrous sulfate as indicated.

TABLE III

| | Repression of β-galactosidase with FeSO$_4$ | |
|---|---|---|
| Plasmid | E. coli M182 | Ps. fluorescens 701E1 |
| pMON5022 +FeSO$_4$ | 1,775 | 8,554 |
| − FeSO$_4$ | 5,033 | 17,449 |

Example 8: Seed Inoculation And Descendant Analyses

Two sets of experiments have been conducted wherein (1) soybean seeds were inoculated with fluorescent pseudomonas transformed with plasmids described above; (2) the seeds were planted in soil, allowed to sprout, and grown for a selected period of time; (3) roots were harvested, and bacteria were collected from the roots and analyzed to determine the number of bacteria containing the plasmids used to transform the inoculated ancestors. One set of experiments was conducted in laboratory conditions; the other set of experiments was conducted in a growth chamber, as described in Example 9.

The laboratory experiments used an assay developed in collaboration with Drs. William Pfender and Arthur Kelman of the University of Wisconsin. Seedling cavity trays (Jiffy Products, Chicago) were cut to individual sections, plugged at the bottom opening with glass wool (enough only to retain soil) and filled to within 1-2 cm of the top with a 50:50 mix of sterile soil (autoclaved 60 minutes and cooled overnight) and fine sand (non-sterile, No. 10 grade). 9 ml distilled water was added to the soil, and excess was allowed to drip from the bottom for 10-15 minutes. A 1.5 ml Eppendorf tube containing 1 ml sterile distilled water was then secured to the cavity bottom so that firm contact was made and the opening was completely covered. Tubes were sealed to the cavity with 1.5% melted agarose placed around the tube lip as a bead with a pasteur pipet. After allowing the agarose to solidify for 2-3 minutes the cavity was submerged in water to a point several cm above the agarose seal to prevent drying.

A small depression (about 2 cm) was made in the soil. A soybean seed (Williams cultivar) which had been soaked in sterile distilled water for 10 minutes was placed in the depression. 50 $\mu$l of the test bacterial culture (100 Klett units; approximately $8 \times 10^8$ cells/ml) was pipetted onto the planted seed, which was then covered with soil. For mixed inoculations, separate cultures were mixed immediately prior to addition to the seed. A layer of fine vermiculite was added, and the cavity top was covered with plastic wrap, which was removed after germination. Trays were placed under growth lights on a 12 hour cycle, and loosely covered with a tent of plastic wrap to maintain constant humidity.

Usually within 5 days, seedlings had germinated and the first tap root had penetrated into the Eppendorf tube, inoculating the sterile water. When the root had grown to the bottom, the tube was carefully removed, and the emerged portion of the root was cut with flamed scissors at the cavity base. The tube was then capped and vortexed with the root section for 15 seconds. Dilution platings of the water were made on Pseudomonas agar F selection media (Difco) containing additives indicated in Table IV. Plates were incubated at 28°-30° C. and colony counts were made within 24-48 hours. To assay colonization of secondary roots, another Eppendorf tube was sealed onto the cavity base immediately after removal of the first tube. Within 2-3 days several secondary roots emerged and inoculated the fresh water or medium. They were harvested and analyzed using similar procedures.

The results of the laboratory test are indicated in Table IV. CFU refers to colony forming units; Km indicates 50 $\mu$g/ml kanamycin; rif indicates 50 $\mu$g/ml rifampicin; X-gal indicates an overspread of 40 $\mu$l of 4% X-gal in dimethyl formamide.

TABLE IV

Plasmid Maintenance In *Ps. fluorescens* 701E1rif-R on Soybean Roots

| Plasmid | Agar additive | Root type | CFR/ml |
|---|---|---|---|
| None | — | Primary | $1.0 \times 10^6$ |
|  | rif | " | $1.9 \times 10^5$ |
|  | — | Secondary | $3.0 \times 10^6$ |

TABLE IV-continued

Plasmid Maintenance In *Ps. fluorescens* 701E1rif-R on Soybean Roots

| Plasmid | Agar additive | Root type | CFR/ml |
|---|---|---|---|
|  | rif | " | $2.3 \times 10^5$ |
| pKT231 | rif | Primary | $2.3 \times 10^5$ |
|  | rif, Km | " | $2.0 \times 10^5$ |
|  | rif, Km | " | $2.0 \times 10^5$ |
| pMON5002 | rif | Primary | $5.3 \times 10^2$ |
|  | rif, Km | " | $5.4 \times 10^2$ |
|  | rif, Km, X-gal | " | $5.5 \times 10^2$ |
|  | rif | Secondary | $5.6 \times 10^4$ |
|  | rif, Km | " | $5.3 \times 10^4$ |
|  | rif, Km, X-gal | " | $5.7 \times 10^4$ |

Example 9: Growth Chamber Trials

Soil was mixed containing 1 part unsterilized soil from St. Charles County, Missouri, 2 parts Terra-lite (W. R. Grace and Co., Cambridge, Mass.) and 1 part of unsterilized sand. The soil mixture was used to fill a growing tray, $12 \times 23 \times 8$ cm. Each tray contained drainage holes in the bottom, and a $22 \times 50$ cm sterile mat in the bottom which aided root recovery.

Seeds were sorted for fungal growth. Selected seeds were surface sterilized with 80% ethanol for 1 minute, blown dry with unheated air, sorted, and placed on the soil surface. Cultures of *Ps. fluorescens* 701E1 rif-R transformed with various plasmids were grown to 200 klett units in M9 media with 1% glucose. 200 $\mu$l of culture solution was pipetted onto the surface of each seed. The seeds were covered with 1 cm soil. Three watering hoses were placed on the top soil on each oblong side of each growing tray. Each hose providing about 7 ml of distilled water four times each day.

The trays were placed in a Model PGV36 (or its equivalent) growth chamber (Controlled Environments, LTD, Winnepeg, Canada). Humidity was constant at 99%; lighting and temperature were 25° C. with four rows of fluorescent lights and 1 row of incandescent light (2700 ft. candles at the tray level) for 14 hours, and 18° C. and no lights for 10 hours each day.

After 7 days, each plant was removed gently from the soil and matting, and shaken to remove most of the soil from the root. Each root was severed, weighed, placed in a 15 ml tube containing 10 ml of sterile water, and shaken for 15 minutes. 100 $\mu$l of the resulting solution was diluted in a 10, 10, 10, 10 series and plated on M9 media containing 1% lactose. Some plates contained ammonium citrate to speed cell proliferation. As indicated in Table V, some plates contained 50 $\mu$g/ml rifamycin, 50 $\mu$g/ml kanamycin, and/or an overspread of 40 $\mu$l of 4% X-gal in dimethyl formamide.

The results are indicated in Tables V and VI. All values are mean values, based upon samples of eight plants.

TABLE V

Relative Colonization Efficiencies of *Ps. fluorescens* 701E1 Strains

| Strain | mean $\times 10^4$ CFU/ml root wash | Medium |
|---|---|---|
| 701E1(no plasmid) | 23 | (1)King's B, rif |
| 701E1(pKT230) | 3.6 | (2)King's B, km |
| 701E1(pMON5003) | 0.47 | (3)Modified M9 with Lactose, km, x-gal |
| Control(no cells) | 0 | Media (1), (2) & (3) |

TABLE VI

Relative Colonization Efficiencies of
Transformed Ps. fluorescens 701E1 Strains

| Strain | mean × $10^4$ CFU/g fresh root weight |
|---|---|
| 701E1(pMON5002) | 3.3 ± 4.9 |
| 701E1(pMON5003) | 0.81 ± 1.00 |
| 701E1(pMON5012) | 1.3 ± 1.1 |
| 701E1(pMON5015) | 2.3 ± 1.8 |
| Control (No cells inoculated) | 0 |

Medium: Modified M9 with lactose, x-gal and Km

REFERENCES

Adams, S. et al, *J. Amer Chem. Soc.* 105:661 (1983)
Alexander, M., *Introduction to Soil Microbiology*, Wiley & Sons, NY (1977)
Allet, B. et al, *Nature* 241: 120 (1973)
Atlas, R. M., and Bartha, R. (eds.) *Microb. Ecol. Fund. And Applications* (1981)
Bagdasarian, M. et al, *Gene* 16:237 (1981)
Bagdasarian, M. et al, *Gene* 26: 273–282 (1983)
Baumberg, S. et al, *J. Gen. Microbiol.* 119: 257–262 (1980)
Becking, J. H. *The Family Azotobacteraceae* (1981)
Bindereif, A. and Neiland, J., *J. Bacteriol.* 153: 1111 (1983)
Bolivar, F. et al, *Gene* 2:75 (1977)
Calos, M. et al, *Cell* 13: 411 (1978)
Casadaban, M., *J. Bacteriol.* 143: 971 (1980a)
Casadaban, M. and Cohen S., *J. Mol. Bio.* 138: 179–207 (1980b)
Cook, R. J. and Baker, K. F. *The Nature and Practice of Biological Control of Plant Pathogens* American Phytopathological Society, St. Paul, Minn. (1983)
Dhawale, S. et al., *Current Genetics* 8: 77–79 (1984)
Figurski, D. and Helinski, D., *Proc. Natl. Acad. Sci.* 76: 1648 (1979)
Griffith, A. J. and Lovitt, R. *Microb. Ecol.* 6: 35–43 (1980)
Hemming, B. C. "Plant-associated fluorescent pseudomonads: their systematic analysis, microbial antagonism and iron interaction." PhD dissertation Montana State University, Bozeman, Mont. 199 pp. University Microfilms, Ann Arbor, Mich. (1982)
Hugh R. and Gibardi, G. L., "Pseudomonas" in *Manual of Clinical Microbiology*, 3rd edition, p. 288–317, American Society for Microbiology (1980).
Ish-Horowicz, D. and Burke, J., *Nucleic Acids Res.* 9: 2989 (1981)
King, E.O. et al, *J. Lab. Clin. Med.* 44: 301–307 (1954)
Kloepper, J. W. and Schroth, M. N. *Phytopathology* 71: 1020–1024 (1981)
Maniatis, T. et al, *Molecular Cloning—A Laboratory Manual* (Cold Spring Harbor Laboratory, 1982)
Mercer, A. and Loutit, J., *J. Bacteriol.* 140: 37 (1979)
Meyer, J. M. and Abdallah, M. A. *J. Gen. Microbiol.* 107: 319–328. (1978)
Miller, J. H. *Experiments in Molecular Genetics* Cold Spring Harbor Lab, NY (1972)
Miller, J. pp. 39, in *The Operon*, J. Miller and W. Reznikoff, eds; Cold Spring Harbor Laboratory, N.Y.; 1978.
Murray, N. et al, *J. Mol. Biol.* 132: 493 (1979)
Sands, D. C. et al., p. 36–44 in *Laboratory Guide for Identification of Plant Pathogenic Bacteria*, American Phytopathological Society, St. Paul, Minn. (1980)
Shelly, D. C. et al., *Clin Chem.* 26: 1127–1132 (1980)
Sneath, P. H. A. and Sokal, R. R. *The Principles and Practice of Numerical Taxonomy*, W. H. Freeman (1973)
Sneath, P. H. A. *J. Gen. Microbiol.* 17: 201–226 (1957)
Sokal, R. R. and Michener, C. D. *Kansas Univer. Science Bulletin* 38: 1409–1438 (1958)
Stuart, S. et al, *J. Bacteriol.* 143: 35 (1980)
Vidaver, A. K., *Appl. Microbiol.* 15: 1523–1524 (1967)
Walczak, C. and Krichevsky *Int. J. of System Bact.* 30(4): 615–621 (1980)
Wishart, D. CLUSTAN User Manual, 3rd Edition, PLU Edinburgh University (1978)
Zabin, I. and Fowler, A. V., Supra, pp. 89 in *The Operon* (supra), 1978.
Zukowski, M. M. et al, *Microbiology* 80: 1101 (1983)

We claim:

1. A method for selecting transgenic fluorescent pseudomonad bacteria from native fluorescent pseudomonad bacteria which comprises genetically transforming the pseudomonad bacteria to be capable of proliferation on media containing lactose as the sole carbon source and culturing a mixed inoculum of native fluorescent pseudomonad bacteria and said transgenic fluorescent pseudomonad bacteria on media containing lactose as the sole carbon source.

2. A method of claim 1 in which the transgenic pseudomonad bacteria is made capable of proliferation on media containing lactose as the sole carbon source by genetically transforming the bacteria to express B-galactosidase.

3. A method of claim 2 in which the bacteria is further transformed to express lactose permease.

4. A method of claim 3 in which the media contains 5-bromo-4-chloro-3-indolyl-β-D-galactopyranoside.

5. A method for tracking fluorescent pseudomonad bacteria in soil which comprises the following steps:
   (a) inoculating soil with a culture of fluorescent pseudomonad bacteria which has been genetically transformed to be capable of proliferation on media containing lactose as the sole carbon source;
   (b) collecting a soil sample; and
   (c) culturing microorganisms recovered from said soil sample on media containing lactose as the sole carbon source; and
   (d) determining the presence of genetically transformed fluorescent pseudomonad bacteria by exposing the proliferated colonies to ultraviolet light having a wavelength of about 290–390 nm.

6. A method of claim 5 in which the fluorescent pseudomonad bacteria is genetically transformed to be capable of proliferation on media containing lactose as the sole carbon source by genetically transforming the bacteria to express B-galactosidase.

7. A method of claim 6 in which the bacteria is further transformed to express lactose permease.

8. A method of claim 7 in which the media of part (c) contains 5-bromo-4-chloro-3-indolyl-β-D-galactopyranoside.

9. An environmental inoculant which comprises a genetically transformed fluorescent pseudomonad bacterium and a carrier material selected from the group consisting of plant parts, seeds, soil, sand, vermiculite, fertilizer and herbicide formulations, said bacterium being transformed to render it capable of proliferation on media containing lactose as the sole carbon source.

10. An environmental inoculant of claim 9 in which the fluorescent pseudomonad bacteria is genetically transformed to be capable of proliferation on media containing lactose as the sole carbon source by genetically transforming the bacteria to express B-galactosidase.

11. An environmental inoculant of claim 9 in which the bacteria is further transformed to express lactose permease.

* * * * *